United States Patent [19]
Lanotte et al.

[11] Patent Number: 5,589,345
[45] Date of Patent: Dec. 31, 1996

[54] CULTURES OF PERMANENT LINES OF HUMAN PROMYELOCYTIC CELLS AND THEIR USES FOR THE SCREENING OF MOLECULES UTILIZABLE IN PARTICULAR IN THE TREATMENT OF LEUKEMIAS

[75] Inventors: Michel Lanotte; Roland Berger, both of Paris, France

[73] Assignee: Institut National de la Sante et de la Recherche Medicale, Paris, France

[21] Appl. No.: 108,587

[22] PCT Filed: Feb. 25, 1992

[86] PCT No.: PCT/FR92/00173

§ 371 Date: Dec. 17, 1993

§ 102(e) Date: Dec. 17, 1993

[87] PCT Pub. No.: WO92/14815

PCT Pub. Date: Sep. 3, 1992

[30] Foreign Application Priority Data

Feb. 25, 1991 [FR] France ................................. 91 02229

[51] Int. Cl.$^6$ ............................. G01N 33/574; C12N 5/08
[52] U.S. Cl. ........................ 435/7.23; 435/6; 435/240.2; 436/63; 436/64; 436/813
[58] Field of Search .............................. 435/7.23, 240.2, 435/6, 243, 41, 975; 436/63, 64, 813, 808

[56] References Cited

FOREIGN PATENT DOCUMENTS

| 143850 | 6/1985 | European Pat. Off. . |
| 63-129994 | 6/1988 | Japan . |

OTHER PUBLICATIONS

Gianni et al, *Blood* 83 (7). 1994. 1909–1921 (abstract only).
Gallagher et al., "Characterization of the Continuous, Differentiating Myeloid Cell Line (HL–60) From a Patient with Acute Promyelocytic Leukemia", *Blood*, 54, 713–733 (1979).
Maizumi et al., "Retinoic Acid–Induced Monocytic Differentiation of HL60–MRI a Cell Line Derived From a Transplantable HL60 Tumor", *Biosis Database Accession* No. 83109596 (1987).

Primary Examiner—Toni R. Scheiner
Assistant Examiner—Yvonne Eyler
Attorney, Agent, or Firm—Merchant, Gould, Smith, Edell, Welter & Schmidt, P.A.

[57] ABSTRACT

The invention concerns permanent cell lines of human promyelocyte cells characteristic of acute promyelocytic leukemias, these cells being cytogenetically characterized by a translocation t(15;17), capable of indefinite proliferation in a culture medium. It also concerns the use of these cell lines, particularly for screening molecules capable of inducing cell maturation.

4 Claims, 2 Drawing Sheets

CULTURES OF PERMANENT LINES OF HUMAN PROMYELOCYTIC CELLS AND THEIR USES FOR THE SCREENING OF MOLECULES UTILIZABLE IN PARTICULAR IN THE TREATMENT OF LEUKEMIAS

This application was filed under 35 U.S.C. 371 as the national stage of PCT/FR92/00173 filed Feb. 25, 1992, and published as WO92/14815 Sep. 3, 1992.

Acute promyelocytic leukemia (or APL or also leukemia type 3) is a well-defined variety of leukemia, and is cytogenetically characterized by a translocation t (15; 17) (q22; q11–12) (Rowley J. D. et al., Lancet 1:549, 1977). This translocation could play a role in the uncontrolled cellular proliferation with blockage of cell maturation which occurs in APL.

In vitro and in vivo studies have made it possible to demonstrate that retinoic acid (also designated hereafter as RA) stops the process of cellular proliferation of the APL and induces the morphological and functional maturation of the promyelocytes towards the granulocyte stage.

This effect of retinoic acid on the promyelocytes suggests that the expression of certain genes intimately implicated in the transduction of the RA signal or in the process of maturation of the cells is adversely affected by the translocation mentioned above.

In vitro studies conducted on promyelocytes derived from patients suffering from APL have made it possible to demonstrate that the gene coding for the alpha receptor of retinoic acid (RARα receptor) normally located on chromosome 17 has been rearranged by translocation with the PML locus normally located on chromosome 15 (de Thé et al., Nature, 347, pp558–561, 1990). By using probes corresponding to segments of DNA localized in the vicinity of the breaking points of the translocation, it was possible to define genomic rearrangements of one or other locus in the patients suffering from APL mentioned above. Consequently, the RARα and PML genes are rearranged in the APLs. These experiments strongly support the implication of the alpha receptor of retinoic acid in acute promyelocytic leukemias.

In the light of the importance of the role played by the RARα in the pathology of the APLs, it would be particularly interesting to be able to have available cell lines constituted of promyelocytes of human origin which have this translocation t (15; 17) characteristic of the APLs in order in particular to screen molecules derived from retinoic acid, or other molecules capable of restoring cell maturation without nonetheless exhibiting the toxic effects of retinoic acid.

However, it has hitherto not been possible to maintain a line of human promyelocytic cells in culture and, consequently, it has not been possible to perform this type of study.

Although the HL60 line has been called "promyelocytic" (Gallagher R. et al., Blood 54:713, 1979), it was subsequently recognized that, on the one hand, it is derived from a myeloblastic leukemia characterized by cells with a certain degree of maturation (M2) (Dalton W. T. et al., Blood 71; 242, 1988) and, on the other, it does not contain the above-mentioned translocation t (15; 17).

One of the objectives of the present invention is precisely that of making available a cell culture which permits the screening of molecules capable of restoring cellular maturation.

The subject of the present invention is permanent cell lines, characterized in that they are constituted essentially of promyelocytic cells characteristic of acute human promyelocytic leukemias, these cells being cytogenetically characterized by a translocation t (15; 17), and capable of proliferating indefinitely in a culture medium.

The culture medium in which the above-mentioned cells are capable of proliferating is advantageously constituted by a synthetic nutrient medium (RPMI 1640) and fetal calf serum.

The cell lines of the invention and their variants are characterized particularly in that they possess DNA fingerprints on gel electrophoresis identical, wholly or in part, with the DNA fingerprint shown in FIG. 1.

As an illustration, the DNA fingerprints of the cells constituting the cell lines of the invention are obtained by the procedure defined in Nucleic Acids Research (1988), vol. 16, No. 9, p. 4161.

The cell lines of the invention are advantageously characterized in that they are either sensitive to retinoic acid, i.e. capable of differentiating from the promyelocytic stage towards the granulocyte stage under the influence of retinoic acid, or, on the contrary, are resistant to retinoic acid and are thus incapable of differentiating under the influence of this latter or also are capable of differentiating as a result of treatment by retinoic acid associated with one or more reducing agents of such differentiation.

The invention relates to a cell line sensitive to retinoic acid (i.e. the majority of the cells of which are capable of differentiating under the influence of this latter), and which was deposited with the Collection Nationale de Culture de Micro-organismes de l'INSTITUT PASTEUR (CNCM) on 25 Feb. 1991 under the number I-1045, as well as with the Deutsche Sammlung von Mikro-organismen und Zellkulturen GmbH (DSM) on 14 Feb. 1992 under the number DSM.ACC.2030.

This cell line was obtained from a patient suffering from an APL, who had been treated by chemotherapy and was in a relapse phase. Cells of the bone marrow were taken from this patient and placed in culture on a layer of cells of the bone marrow stroma (Lanotte et al., J. Cell. Sci. 50:281, 1981) until an autonomous cell line was established (designated hereafter by the expression NB4). This cell line NB4 is characterized in particular by the DNA fingerprint shown in FIG. 1, and is constituted mainly of cells sensitive to retinoic acid. It forms the subject of a more thorough study in the detailed description of the invention which follows.

The subject of the invention is also a cell line resistant to retinoic acid (i.e. the majority of the cells of which are incapable of differentiating under the influence of the latter), this line (designated hereafter by the expression NB4R) being obtained by incubation of the previously mentioned NB4 line in the presence of all-trans retinoic acid, followed by the isolation of the resistant cells and the amplification of these latter still in the presence of retinoic acid.

The invention also relates to a screening procedure for molecules capable of restoring cellular maturation, and more particularly of inducing the maturation of the promyelocytes towards the granulocyte stage, in particular in the context of acute human promyelocytic leukemias, this procedure being characterized in that it comprises the placing of a specific quantity of the molecule under study in contact with a cell line of the invention, and more particularly with a sensitive cell line, followed by the detection of possible differentiation of the cells of the said line.

The subject of the invention is also a screening procedure for molecules capable of abolishing the resistance which the cells exhibit, and more particularly cells characteristic of the acute human promyelocytic leukemias, to the effect on differentiation of retinoic acid or other compounds normally capable of inducing cell maturation but for which phenomena of resistance by the cells concerned may be observed, the said procedure being characterized in that it comprises the placing of a specific quantity of the molecule under study in contact with a resistant cell line such as defined above, followed by the detection of possible differentiation of the cells of the said line in the presence of retinoic acid or of the other compounds mentioned above.

The above-mentioned procedure advantageously makes it possible to select molecules which are capable of abolishing this phenomenon of resistance mentioned above, on the one hand, and of restoring cellular maturation under the above-mentioned conditions, on the other.

In the context of the procedures mentioned above, the detection of the differentiation of the promyelocytes of the cell lines of the invention towards the granulocytic stage is advantageously carried out by application of one or more of the following methods.

Since this differentiation is expressed in particular by the activation of the expression of certain specific genes, the expression products of these genes are detected with the aid of specific antibodies, these antibodies being labelled if necessary, in particular radioactively or enzymatically.

When these expression products exhibit an enzymatic activity or when this maturation is expressed by a disappearance of an enzymatic activity such as myeloperoxidase activity, the detection of the differentiation is advantageously achieved with the aid of substrates, labelled if necessary, in particular radioactively or enzymatically, on which the enzymatically active products expressed, or which are no longer expressed, are capable of acting.

The detection of this cellular differentiation may also be carried out by a morphological study of the cells, in particular after staining of the latter. As an example of a staining method for the cells, mention may be made of the May-Grünwald-Giemsa stain.

Cellular differentiation may also be assessed according to a functional criterion, i.e. a study is made as to whether the differentiated cells are functional in the same way as normal granulocytes. As an example of a test capable of making possible the detection of functional criteria of normal granulocytes, mention should be made of the NBT (Nitro Blue Tetrazolium) test (Pick E., Methods Enzymol. 133:407, 1986).

The response time of the cell lines of the invention to the molecules under study when used in the procedures described above varies from several hours to several days depending on the method of detection of cellular differentiation selected.

As an illustration, the incubation time necessary before detection of the activation of the expression of genes is of the order of 30 minutes to 24 hours, that necessary prior to detection of the modification of the morphological aspect of the cells varies from 15 hours to 5 days, and that necessary prior to detection of the functional aspect of the cells varies from 3 days to 7 days.

Advantageously, these screening methods make it possible to select molecules capable of being used in the area of the prevention or treatment of diseases caused by an abnormal proliferation of the cells, in particular malignant tumors in general, and more particularly leukemias, especially acute promyelocytic leukemias.

More particularly in the case when cell lines resistant to retinoic acid are used, these methods make possible the selection of molecules capable of being used in the context of the prevention of the appearance of resistance phenomena directed against the differentiation effect of retinoic acid or other compounds normally capable of inducing cell maturation of the cells of a patient when this latter is being treated with retinoic acid or compounds mentioned above.

Still in the context of the use of cell lines resistant to retinoic acid, these procedures according to the invention make possible the selection of molecules capable of being used in the context of the treatment of patients in relapse after treatment with retinoic acid or other compounds normally capable of inducing cell maturation.

The invention also relates to the cultures themselves constituted by cells of the cell lines of the invention, particularly the NB4 or NB4R cells mentioned above, and a nutrient support enabling the cells to proliferate, in particular the RPMI 1640 medium supplemented with fetal calf serum indicated above.

Consequently, the subject of the invention is kits for the implementation of the screening procedures such as those described above, these kits containing:

a culture such as that described above comprising a cell line according to the invention, suitable reagents for the detection of the possible differentiation of the cells, in particular:

* antibodies capable of recognizing specifically the polypeptides produced by the activation of the expression of certain genes, these antibodies being labelled if necessary, in particular radioactively or enzymatically,

* substrates, labelled if necessary, in particular radioactively or enzymatically, on which the enzymatically active products, expressed or which are no longer expressed, are capable of acting,

* enzymes, labelled if necessary, in particular radioactively or enzymatically, and capable of acting on substrates produced during cellular differentiation,

* cell stains.

The cell lines of the invention are also characterized in that the surface membranes of the cells constituting them are recognized in particular by all of the antibodes directed specifically against antigens of human leukocyte membranes of class I (HLA class I), the markers CD13 and CD33 of the myeloid cells, the markers CD15 and CD11b of the granulocytes, the markers CD9 and CD11B of the monocytes, the marker CD11b of alpha-integrin, the marker CD38 of the activated T cells, the marker CD2 of the T cells, the marker CD4 of the HIV receptor of the T helper cells, respectively, or are recognized by some of them only, but are not recognized by the antibodies directed against the antigens of human leukocyte membranes of class II (HLA class II), the marker CD10 of the antigens of the leukocyte surface membrane of acute lymphocytic leukemias (CALLA), the markers CD11c, CD14, CD36 of the monocytes, the marker CD36 of the platelets, the marker CD7 of the immature T cells, the marker CD3 of the T cells, the beta chain of the IL-2 cell receptor, the marker CD19 of the B Pan cells, the CD23 marker of the mature B cells, the marker CD34 of the precursor cells of the lymphocytes and myelocytes, the marker CD41 of the platelets of group II/IIIa, the marker CD42 of the platelets of group IX, the erythrocytes, glycophorin, or are not recognized by some of them only.

The presence of the marker CD4 at the surface of the cells of the invention confers on these latter the property of being a model of choice for the study of the process of the infection of the cells by the viruses of the HIV type.

The subject of the present invention is also the use of the above-mentioned cell lines as positive controls in the context of in vitro diagnostic procedures for acute human promyelocytic leukemias or also the use of the resistant cell lines described above as positive controls in the context of in vitro diagnostic procedures for the possible appearance of cells resistant to retinoic acid or other compounds capable of inducing the cell maturation during the treatment of a patient with these compounds.

The invention also relates to kits for the implementation of the in vitro diagnostic procedures for acute human promyelocytic leukemias, these kits containing a cell line selected from those described above as positive control of the presence of cells characteristic of acute human promyelocytic leukemias.

The invention also relates to kits for the implementation of in vitro diagnostic procedures for the possible appearance of cells resistant to retinoic acid or other compounds capable of inducing cell maturation during the treatment of a patient with these compounds, these kits containing a resistant cell line selected from those described above as positive control of the presence of cells resistant to the compounds mentioned above.

The subject of the present invention is also polypeptides produced by the cell lines of the invention, whether they are secreted or not, and implicated in the mechanism of autonomous proliferation of the cells of these lines.

These polypeptides, growth factors for example, are obtained from the cell lines of the invention, in particular according to the method comprising the following steps:

- incubation of the cells of the lines of the invention in a culture medium,
- withdrawal of a sample of the incubation medium and detection of the possible presence of one or more polypeptides such as defined secreted into the medium with the aid of a proliferation and differentiation test carried out on reference hematopoietic cells, or on the lines NB4 and NB4R or their variants,
- biochemical separation (chromatography, electrophoresis, etc. . . ) of the polypeptide(s) mentioned above.

These steps described above lead to the production of the natural molecule(s).

The production of the recombinant molecule(s) may be carried out by screening an expression library of the lines NB4 and NB4R or a variant of these lines producing the desired biological activity, followed by genetic cloning and the production of the above-mentioned recombinant molecule(s).

The subject of the invention is more particularly the growth factor(s) derived from the cell lines NB4 and NB4R, and capable of being obtained according to the procedure indicated above.

The invention will be illustrated more particularly with the aid of the detailed description which follows of the production of the cell line NB4 and the cell line NB4R.

I MATERIALS AND METHODS a) Cell culture and establishment of the cell line NB4

A sample of bone marrow was taken from a patient suffering from APL after this patient had received treatment with retinoic add. The leukocytes were separated by centrifugation on Ficoll-Hypaque and cultured at a concentration of $10^4$ cells/ml on a nutrient support constituted of cells of human bone marrow stroma (Lanotte et al., J. Cell Sci. 50:281, 1981), with a RPMI 1640 medium (GIBCO, Grand Island, N.Y.) supplemented with 12.5% fetal calf serum (FCS), 7.5% horse serum (Flow Lab, Scotland) in a plastic bottle at 37° C. in moist air plus 5% $CO_2$. The cultures were maintained by replacing one half of the growth medium each week with fresh medium. After 4 to 5 weeks, the adherent layer containing regions of proliferating leukemic cells was detached mechanically and the entire cell population was transferred without dissociation to a bottle containing a fresh nutrient support consisting of cells of bone marrow stroma. In this way a progressive enrichment of proliferating APL cells was obtained. Development was observed during fourteen weeks, depending on the microenvironment. Autonomous growth was then detected and a rapidly developing cell population invaded the culture and became a cell line. The APL cells thus obtained are designated NB4. The NB4 growth conditions were improved by culturing the cells at a concentration of $2 \times 10^5$ cells/ml in a RPMI 1640 medium supplemented with 10% FCS only (the doubling time varies from 36 to 40 hours). Aliquot quantities of cells were frozen at −80° C.

b) Cytogenetic analysis

The chromosomes were studied when the cell line had been established and after 40 weeks of culture with 2 passages per week. The R bands procedure (RHG) was used and the chromosomes were classed according to the international nomenclature (ISCN/1985/: An International System for Human Cytogenetic Nomenclature) (Harnden D. G., Klinger H. P./eds/Published in collaboration with Cytogenet Cell Genet. Basel, Switzerland, Karger, 1985).

c) Induction of differentiation

The NB4 cells ($10^5$ cells/ml) in RPMI medium containing 10% FCS and variable concentrations of all-trans retinoic acid (Sigma) as inducing agent were incubated for 1 to 5 days on culture microplates. The maturation was assessed by microscopic examination of the enzymatic staining on the cytological plates and also by the adhesion of the cells of the stroma to the extracellular matrix, fibronectin. The cells were stained with the aid of May-Grünwald-Giemsa. The reactions were carried out with myeloperoxidase, alpha-naphthyl butyrate esterase, naphthol-ASD chloroacetate esterase, alkaline phosphatase and with NBT.

d) Cell surface markers

The staining of the cell suspensions in the case of indirect immunofluorescence was carried out according to the methods described in (Chen Z. et al.: Immunological typing of ALL: Concurrent analysis by flow cytometry and immunocytology. Leuk Res. 10:1411, 1986). The cytofluorometric analysis was carried out on an EPICS profile (Coultronics, Margency, France). A large number of monoclonal antibodies was used (cf. above).

II RESULTS a) Establishment, morphology and cytometry of the cell line.

The APL cells were cultured on a layer of cells of the stroma of bone marrow. At the start of the culture a subpopulation of cells having achieved a certain "cooperation" with the hematopoietic microenvironment was selected. The total population, with interaction losses with the cells of the stroma, was constituted of hypergranular promyelocytes in the G0/G1 phase, whereas some leukemic cells strongly associated with the cells of the stroma had a mitotic activity and were much less granular with the morphology of the blast cells found in the APLs. At the time when the NB4 cell line was isolated, only the blast cells proliferated. After 9 months of culture (i.e. about 155 cell doublings) no significant change was observed.

b) Cytogenetic study

The cytogenetic analyses were performed at the initial stage of the culture when the NB4 cell line was isolated, and after nine months of culture. At the initial stage of culture, the 23 metaphases examined were abnormal with caryotypic variations from one cell to another. The number of their chromosomes varied between 68 and 90, most of them being located in the hypotetraploid region, with random losses.

All of the metaphases have the translocation t (15; 17) (q22; q11–12) associated with other rearrangements varying from one cell to another. However, a loss of chromosome 19 and a replacement by 19q+, on the one hand, and a der (12; ?) (p 12; ?) was present in all of the metaphases examined.

The translocation t (15; 17) present in the first caryotype conducted on the patient suffering from APL mentioned above and at the stage of his second relapse was observed in all of the metaphases of the established cell line. The caryotypic complexity which was observed in the culture of bone marrow in the short-term was found in the cell line with a great variation from one cell to another. The caryotype was hypotetraploid with loss of at least one copy of the chromosomes 8, 11 and 14. A representative caryotype may be summarised in the following manner:
80–87, XXX, –X, –3, –8, –9, –10, –12, –14, –14, –18, –19, –19, der (12), t (12;?) (p12;), t (15; 17) (q22; q11–12), t (15; 17), der (19) t (19; ?), + variable markers.

In view of this variation, it is difficult to establish the minor differences between the caryotypes of the "fresh" cells and the caryotypes of the cells of the NB4 line. However, it was possible to detect a new marker der (12) in the cell line whereas it was not present in the "fresh" cells. The rearrangement of the chromosome 19, resembling HSR (19) (q13), which is found in certain metaphases of the "fresh" cells, was apparently selected during the establishment of the cell line since it was present in all of the metaphases, most of the time in duplicate.

The caryotype of the NB4 line is shown in FIG. 2.

c) Immunocytological analysis

The cell surface markers of NB4 were analysed (cf.above) and monitored for 9 months, but no significant change was detected. It was thus determined that NB4 expresses specific markers at the granulocytic stage, but also lymphoid cell markers such as CD2, CD4 and a monocyte marker CD9. The percentages of the positive cells compared with the myeloid markers (73% to 89%) and T cell markers (73% for CD4) suggest that the characteristics of the two lines are expressed simultaneously. CD9 is expressed by 73% of the cells, whereas the cells are clearly negative with respect to the other markers associated with the monocyte such as CD14 and CD36. The expression of these antigens might be associated with activations of genes linked to the alterations of multiple caryotypes which were found.

d) Retinoic acid induces maturation

NB4 cells were treated with trans retinoic acid (1 umol/l) for six days. The cessation of cellular proliferation occurred 48 hours later; morphological maturations accompanied by modifications of the surface antigens and functional markers can be detected. A large increase in the marker correlated with alpha-integrin, CD11b (Arnaout M. A.: Structure and function of the leukocyte adhesion molecules CD11 CD18. Blood 75:1037, 1990) was observed; CD11c, which is absent from blast cells is strongly expressed on 75% of the differentiated cells; these changes are associated with a marked increase in the adhesion of the cells to the extracellular matrices. The production of superoxide and hydrogen peroxide, and the reduction of the NBT were analysed quantitatively by ELISA and by cytochemical methods; a large increase in the positivity of the NBT test indicates a potential and microbial capacity confirming the morphological maturation induced by the retinoic acid.

III ANALYSIS OF THE RESULTS

The NB4 cell line is the only permanent line exhibiting a translocation t (15; 17) which has been established from leukemic cells of a patient suffering from APL.

The cells derived from human APLs (M3) exhibit a remarkable manner of proliferating in vitro which is the probable reason for the failures hitherto to obtain a permanent cell line. It may be concluded from these failures: (1) that the APL cells have a very low proliferation potential in vitro. The analysis of the cell cycle by means of cytometry shows a cessation of the proliferation in the G1 phase (or possibly in phase G0) for several weeks, during which the cells become hypergranular and exhibit an intense myeloperoxidase reaction. However, the APL cells survive in culture, whereas many cellular types of leukemias die; that suggests that these cells do not require survival factors, as distinct from normal promyelocytes or cell lines dependent on factors. (2) none of the hematopoietic growth factors tested so far (including G-CSF) leads to in vitro proliferation for more than 3 to 4 cycles. (3) the APL cells undergo cell-cell or cell-matrix interactions with the cells of the stroma of the bone marrow. Some APL cells associated with the micro-environment (1 to 10 per $10^5$ cells) proliferate.

In the light of what has just be stated it might be expected that APL cells co-cultured with bone marrow stroma for several months could lead to the selection of cells capable of proliferating. The authors of the present patent application have put forward the hypothesis that the isolation of a permanent APL cell line depends on a second event responsible for the autonomy of proliferation and that its probability should be considerably increased in a population undergoing cyclic growth as compared to a population arrested at stage G1. This strategy was adopted in order to isolate the NB4 cell line. The primary culture of leukemic cells on a layer of stroma cells provides a favourable environment for cell proliferation. It cannot be asserted that an additional mutation is responsible for the appearance of autonomous leukemic cells which develop in the culture of APL cells depending on the microenvironment. It should be emphasized that an additional marker der (12) is present in the cell line but cannot be detected in the "fresh" cells. On the other hand, a self-renewing cell population might already be present in the bone marrow of the patient and would be capable of being selected in vitro. Several observations support this latter hypothesis: (1) Among the multiple chromosomal changes in the blast cells of the patient, which are perhaps partially related to prior treatments, some rearrangements favouring in vitro proliferation may have been selected. (2) The NB4 cells have conserved morphological characteristics of a minority population of blast cells which was also found in the patient at the time of his relapse.

The retinoic acid induces a rapid maturation of the NB4 cells from the morphological and functional point of view; after 3 days of continuous treatment with retinoic acid cell proliferation is no longer detectable. The maturation of the NB4 cells with other inducers such as phorbol esters, dimethyl sulfoxide, cyclic nucleotides and corticosteroids never equals in intensity and rapidity the maturation induced by retinoic acid.

IV ESTABLISHMENT OF THE NB4R LINE

Figure 1:
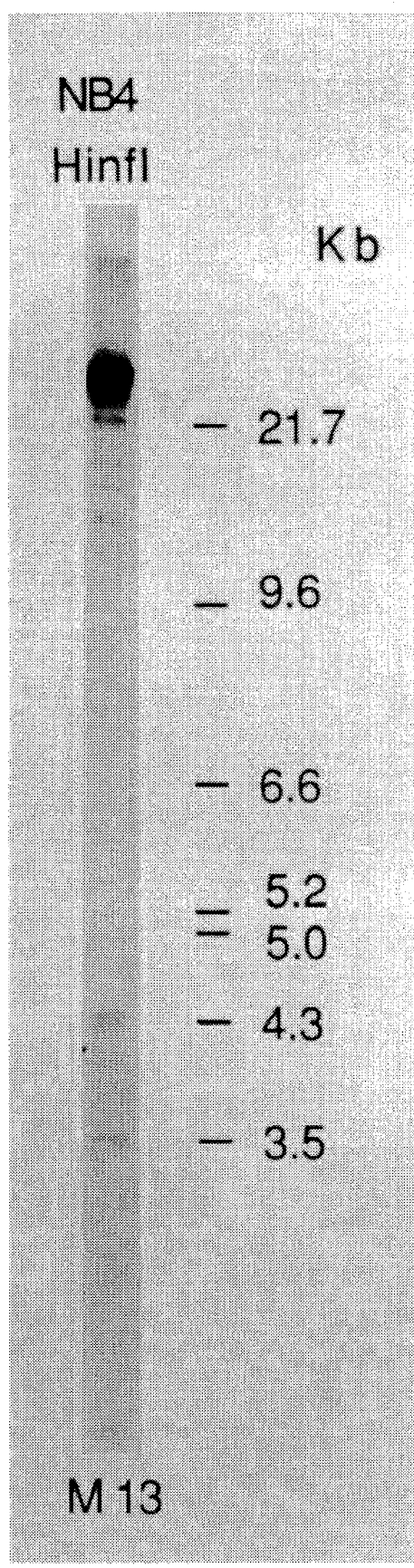
FIG. 1 shows the DNA fingerprint of the NB4 cell line, and which is obtained by digestion of the genome of the cells with HinfI, followed by migration of the DNA fragments obtained in gel electrophoresis and detection of fragments with the aid of the probe M13 (cf. Nucleic Acids Research mentioned above).

Cells of the initial isolate of the human promyelocytic line NB4 were incubated in the continuous presence of all-trans retinoic acid: after several months of culture, some resistant cells were isolated and amplified constantly in the presence of retinoic acid. This isolate has made it possible to isolate a NB4 cell line resistant to retinoic acid (NB4R line). The resistant cells constitute an autonomous line, permanent in the same way as the sensitive NB4 line and which can be maintained under the same conditions. It is interesting to note that this resistance corresponds to a commonly observed clinical fact, namely the relapse after a quite prolonged remission following treatment with retinoic acid. The patient from whom these lines are derived was himself in relapse after chemotherapy and treatment by retinoic acid. Hence it is possible to say that the two isolates NB4 and NB4R, one sensitive to retinoic acid, the other resistant, represent two parts of this disease. These cells make it possible to study the mechanism of acquisition of resistance to the treatment of promyelocytic leukemias by retinoic acid. This complementarity reinforces the interest in the tool which these lines constitute for the study of the effects of the therapeutic agents and for the research of agents to prevent (or abolish) resistance to these agents. The resistant line constitutes the only existing biological model of a promyelocytic line with t (15; 17) enabling molecular screening to be carried out in order to discover novel medicines active on the cells of patients in relapse after treatment with retinoic acid.

We claim:

1. A permanent cell line of human promyelocytic cells designated NB4, wherein the cell line NB4 was deposited with the Collection Nationale de Culture de Micro-organismes de l'INSTITUT PASTEUR (CNCM) on Feb. 25, 1991 under accession number I-1045, and with the Deutsche Sammlung von Mikro-organismen und Zellkulturen GmbH (DSM) on Feb. 14, 1992 under accession number DSM.ACC.2030.

2. The cell line according to claim 1, wherein the cells exhibit DNA fingerprints on an electrophoresis gel identical, in whole or in part, with the DNA fingerprint shown in FIG. 1.

3. The cell line according to claim 1, wherein the cell line comprises a cell culture in association with nutrient elements enabling cells of the cell culture to proliferate.

4. A kit for a method for in vitro screening of acute human promyelocytic leukemia utilizing an NB4 cell line as a positive control, wherein the cell line NB4 was deposited with the Collection Nationale de Culture de Micro-organismes de l'INSTITUT PASTEUR (CNCM) on Feb. 25, 1991 under accession number I-1045, and with the Deutsche Sammlung von Mikro-organismen und Zellkulturen GmbH (DSM) on Feb. 14, 1992 under accession number DSM.ACC.2030, said kit comprising:

(a) an NB4 cell line; and (b) a reagent suitable for detection of cellular differentiation.

* * * * *

UNITED STATES PATENT AND TRADEMARK OFFICE
CERTIFICATE OF CORRECTION

PATENT NO. : 5,589,345

DATED : December 31, 1996

INVENTOR(S) : Lanotte et al.

It is certified that error appears in the above-identified patent and that said Letters Patent is hereby corrected as shown below:

Col. 1, line 51: insert --SUMMARY OF THE INVENTION-- before the paragraph that begins "Although the HL60".

Col. 5, line 50: insert --BRIEF DESCRIPTION OF THE DRAWINGS

FIG. 1 shows the DNA fingerprint of the NB4 cell line, and which is obtained by digestion of the genome of the cells with Hinfl, followed by migration of the DNA fragments obtained in gel electrophoresis and detection of fragments with the aid of the probe M13 (cf. Nucleic Acids Research mentioned above).

Figure 2:
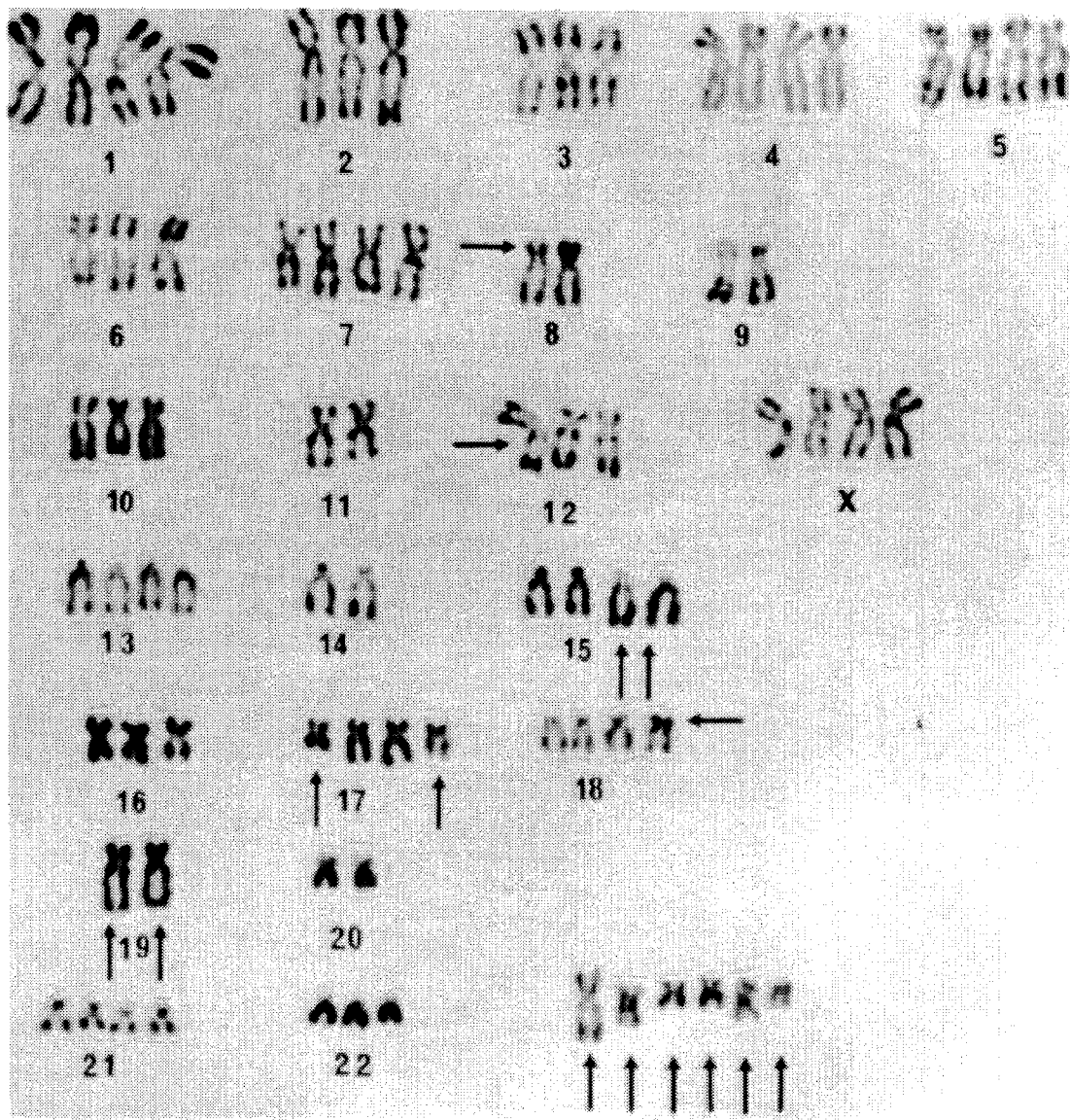
FIG. 2 shows the caryotype of the NB4 cell line, the arrows indicate the rearranged chromosomes.

FIG. 2 shows the caryotype of the NB4 cell line, the arrows indicate the rearranged chromosomes.

DETAILED DESCRIPTION OF THE INVENTION--

Col. 5, line 56: "add" should read --acid--

Col. 7, line 61: "microbial" should read --antimicrobial--

Signed and Sealed this

Thirteenth Day of January, 1998

Attest:

BRUCE LEHMAN

*Attesting Officer*    *Commissioner of Patents and Trademarks*